United States Patent
Takeda et al.

(10) Patent No.: US 11,084,787 B2
(45) Date of Patent: Aug. 10, 2021

(54) METHOD FOR PRODUCING 1-METHYLPYRROLIDIN-3-OL

(71) Applicants: SUMITOMO CHEMICAL COMPANY, LIMITED, Tokyo (JP); KAKEN PHARMACEUTICAL CO., LTD., Tokyo (JP)

(72) Inventors: Masahiro Takeda, Osaka (JP); Yohei Tanaka, Osaka (JP)

(73) Assignees: SUMITOMO CHEMICAL COMPANY LIMITED, Tokyo (JP); KAKEN PHARMACEUTICAL CO., LTD., Tokyo (JP)

( * ) Notice: Subject to any disclaimer, the term of this patent is extended or adjusted under 35 U.S.C. 154(b) by 593 days.

(21) Appl. No.: 16/076,185

(22) PCT Filed: Feb. 9, 2017

(86) PCT No.: PCT/JP2017/004661
§ 371 (c)(1),
(2) Date: Aug. 7, 2018

(87) PCT Pub. No.: WO2017/138588
PCT Pub. Date: Aug. 17, 2017

(65) Prior Publication Data
US 2021/0179555 A1   Jun. 17, 2021

(30) Foreign Application Priority Data
Feb. 10, 2016 (JP) .............................. JP2016-023518

(51) Int. Cl.
*C07D 207/12* (2006.01)
*B01J 23/42* (2006.01)
*B01J 23/44* (2006.01)

(52) U.S. Cl.
CPC ............ *C07D 207/12* (2013.01); *B01J 23/42* (2013.01); *B01J 23/44* (2013.01)

(58) Field of Classification Search
None
See application file for complete search history.

(56) References Cited

U.S. PATENT DOCUMENTS

| 4,713,454 | A | 12/1987 | Sakai et al. |
| 5,359,076 | A | 10/1994 | Kohno et al. |
| 6,420,375 | B1 | 7/2002 | Aono et al. |
| 8,188,301 | B2 | 5/2012 | Sonesson et al. |
| 2005/0282875 | A1 | 12/2005 | Prat Quinones et al. |
| 2007/0129420 | A1 | 6/2007 | Quinones et al. |

FOREIGN PATENT DOCUMENTS

| CN | 104744271 A | 7/2015 |
| ES | 2206021 B1 | 8/2005 |
| JP | S61-172877 A | 8/1986 |
| JP | H05-125052 A | 5/1993 |
| JP | H10-291981 A | 11/1998 |
| JP | 2004-244418 A | 9/2004 |
| JP | 2009-040725 A | 2/2009 |
| JP | 2009-105193 A | 6/2014 |
| WO | WO 2003/087094 A2 | 10/2003 |
| WO | WO 2003/091209 A1 | 11/2003 |

(Continued)

OTHER PUBLICATIONS

WO-2003091209, machine translation from Google Patents downloaded Apr. 24, 2021.*

(Continued)

*Primary Examiner* — Clinton A Brooks
(74) *Attorney, Agent, or Firm* — Leydig, Voit & Mayer, Ltd.

(57) ABSTRACT

The invention relates to a method of producing compound (I)

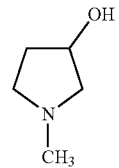

by (A) reacting compound (II)

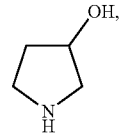

formaldehyde and hydrogen in the presence of a metal catalyst, in a solvent, wherein the amount of the formaldehyde to be used is exceeding 1 mol and not exceeding 5 mol per 1 mol of compound (II), to obtain a mixture containing the formaldehyde and compound (I), and (B) mixing the obtained mixture containing the formaldehyde and compound (I) with hydrogen and a secondary amine selected from the group consisting of diethylamine, dipropylamine, diisopropylamine, butylethylamine, pyrrolidine, piperidine and morpholine, in the presence of a metal catalyst, in a solvent, and then removing the metal catalyst, followed by obtaining the compound (I) by distillation.

4 Claims, No Drawings

(56) References Cited

FOREIGN PATENT DOCUMENTS

WO    WO 2007/059021 A1    5/2007

OTHER PUBLICATIONS

Japanese Patent Office, International Search Report in International Patent Application No. PCT/JP2017/004661 (dated Apr. 18, 2017) English abstract.
Bekkali et al., "Identification of a novel class of succinyl-nitrile-based Cathepsin S inhibitors," Bioorg. Med. Chem. Lett., 17(9): 2465-2469 (2007).
European Patent Office, Extended European Search Report in European Patent Application No. 17750309.1 (dated Sep. 17, 2019).

* cited by examiner

METHOD FOR PRODUCING 1-METHYLPYRROLIDIN-3-OL

CROSS-REFERENCE TO RELATED APPLICATIONS

This patent application is the U.S. national phase of International Patent Application No. PCT/JP2017/004661, filed Feb. 9, 2017, which claims the benefit of Japanese Patent Application No. 2016-023518, filed on Feb. 10, 2016, which are incorporated by reference in their entireties herein.

TECHNICAL FIELD

The present invention relates to production of 1-methylpyrrolidin-3-ol.

BACKGROUND ART

1-Methylpyrrolidin-3-ol is useful as an intermediate for producing a medicament (e.g., Patent Document 1). Patent Document 1 describes in Example 1 that (S)-3-hydroxypyrrolidine and 37% aqueous formaldehyde solution were reacted in the presence of 10% palladium on carbon and hydrogen, in water, and the palladium on carbon was removed by filtration, and the filtrate was distilled to obtain (S)-1-methyl-3-hydroxypyrrolidine in 31% yield.

DOCUMENT LIST

Patent Document

Patent Document 1: WO 03/091209

SUMMARY OF THE INVENTION

Problem to be Solved by the Invention

The aim of the present invention is to provide a production method of 1-methylpyrrolidin-3-ol on an industrial scale.

Means of Solving the Problem

The present inventors have conducted intensive studies in an attempt to solve the above-mentioned problem, and resulted in the completion of the present invention.

Accordingly, the present invention provides the following.

[1] A method of producing a compound represented by the formula (I) (hereinafter sometimes to be referred to as compound (I)):

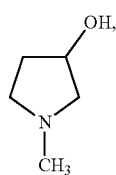
(I)

which comprises

Step A: a step of reacting a compound represented by the formula (II) (hereinafter sometimes to be referred to as compound (II)):

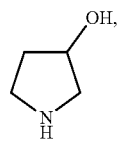
(II)

formaldehyde and hydrogen in the presence of a metal catalyst, in a solvent, wherein the amount of the formaldehyde to be used is exceeding 1 mol and not exceeding 5 mol per 1 mol of the compound represented by the formula (II), to obtain a mixture containing the formaldehyde and the compound represented by the formula (I), and Step B: a step of mixing the obtained mixture containing the formaldehyde and the compound represented by the formula (I) with hydrogen and a secondary amine selected from the group consisting of diethylamine, dipropylamine, diisopropylamine, butylethylamine, pyrrolidine, piperidine and morpholine, in the presence of a metal catalyst, in a solvent, and then removing the metal catalyst, followed by obtaining the compound represented by the formula (I) by distillation.

[2] The method of the above-mentioned [1], wherein the amount of the secondary amine to be used is (X-1) to (10X-10) mol when the amount of the formaldehyde to be used is X mol per 1 mol of the compound represented by the formula (II).

[3] The method of the above-mentioned [1], wherein the amount of the formaldehyde to be used is 1.05 to 2.0 mol per 1 mol of the compound represented by the formula (II).

[4] The method of the above-mentioned [1], wherein the metal catalyst is palladium on carbon or platinum on carbon.

Effect of the Invention

According to the present invention, 1-methylpyrrolidin-3-ol can be produced on an industrial scale.

DESCRIPTION OF EMBODIMENTS

Step A and Step B are explained in detail in the following.

In Step A, compound (II), formaldehyde and hydrogen are reacted in the presence of a metal catalyst, in a solvent, wherein the amount of the formaldehyde to be used is exceeding 1 mol and not exceeding 5 mol per 1 mol of compound (II), to obtain a mixture containing the formaldehyde and compound (I).

Compound (II) is pyrrolidin-3-ol, and it can be (3R)-pyrrolidin-3-ol, (3S)-pyrrolidin-3-ol, or mixtures thereof.

Compound (I) is 1-methylpyrrolidin-3-ol, and it can be (3R)-1-methylpyrrolidin-3-ol, (3S)-1-methylpyrrolidin-3-ol, or mixtures thereof.

Formaldehyde is used as paraformaldehyde or a 10%-50% aqueous formaldehyde solution. The amount of the formaldehyde to be used is, on formaldehyde conversion, exceeding 1 mol and not exceeding 5 mol, preferably 1.05 to 2.0 mol, per 1 mol of compound (II), in terms of yield and economics.

Examples of the solvent include hydrophilic solvents, specifically $C_{1-4}$ alcohols such as methanol, ethanol, 1-propanol, 2-propanol, tert-butanol and the like; water; and mixed solvents thereof. Among them, methanol, water, and mixed solvents thereof are used preferably, in terms of reactivity and yield. The amount of the solvent to be used is, in terms of yield and economics, generally 0.5 to 20 parts by weight, preferably 3 to 7 parts by weight from industrial aspect, per 1 parts by weight of compound (II).

Examples of the metal catalyst include catalysts containing a platinum group metal (palladium, platinum, ruthenium, rhodium, iridium and osmium), preferably specifically palladium catalysts such as palladium on carbon, palladium on alumina, palladium hydroxide, palladium on calcium carbonate, palladium on barium sulfate, palladium black etc.;

platinum catalysts such as platinum on carbon, platinum on alumina, platinum oxide, platinum black etc.; and the like. Among them, preferred are platinum on carbon and palladium on carbon, particularly preferred is platinum on carbon, in terms of reactivity and yield.

The amount of the metal catalyst to be used is, on conversion of the metal contained in the catalyst, preferably 0.0005 to 0.01 parts by weight, per 1 parts by weight of compound (II), in terms of yield and economics.

The reaction is carried out under hydrogen atmosphere, and the hydrogen pressure is generally normal pressure (0.1 MPa)-1 MPa.

The reaction is carried out by mixing compound (II), formaldehyde, a metal catalyst and a solvent, under hydrogen atmosphere.

While the reaction temperature varies depending on the kind of the solvent, it is within the range of preferably 10° C.-100° C., more preferably 10 to 50° C. The reaction time is about 2 to 30 hr.

The completion of the reaction can be confirmed by disappearance of the raw material, using thin layer chromatography, gas chromatography and the like.

After the completion of the reaction, the post-treatments such as removal of the metal catalyst from the reaction mixture, evaporation of the solvent, and the like may be performed. Since the metal catalyst, hydrogen and solvent are also used in Step B, Step B preferably follows the completion of the reaction.

In Step B, the mixture containing the formaldehyde and compound (I) is mixed with hydrogen and a secondary amine selected from the group consisting of diethylamine, dipropylamine, diisopropylamine, butylethylamine, pyrrolidine, piperidine and morpholine, in the presence of a metal catalyst, in a solvent, and then the metal catalyst is removed, and then the compound (I) is obtained by distillation.

The secondary amine may be used alone or in combination of two or more kinds thereof. The secondary amine is preferably diethylamine, in terms of purity and yield of the product.

The amount of the secondary amine to be used is within the range of preferably (X-1) to (10X-10) mol, more preferably (X-1) to (5X-5) mol, still more preferably (X-1) to (3X-3) mol, in terms of yield and economics, when the amount of the formaldehyde to be used is X mol per 1 mol of compound (II).

Examples of the metal catalyst include those exemplified in Step A. The amount of the metal catalyst to be used is, on conversion of the metal contained in the catalyst, preferably 0.0005 to 0.01 parts by weight, per 1 parts by weight of compound (II), in terms of yield and economics.

When Step B follows the completion of Step A, additional metal catalyst does not need to be used.

Examples of the solvent include those exemplified in Step A. The amount thereof to be used is, in terms of yield and economics, generally 0.5 to 20 parts by weight, preferably 3 to 7 parts by weight from industrial aspect, per 1 parts by weight of compound (II). When Step B follows the completion of Step A, additional solvent does not need to be used.

The reaction is carried out under hydrogen atmosphere, and the hydrogen pressure is generally normal pressure (0.1 MPa)-1 MPa.

While the reaction temperature varies depending on the kind of the solvent, it is within the range of preferably 10° C.-100° C., more preferably 10 to 50° C. The reaction time is about 1 to 80 hr.

The completion of the reaction can be confirmed by disappearance of the raw material, using thin layer chromatography, gas chromatography and the like.

The metal catalyst is removed from the obtained reaction mixture, and the compound (I) is obtained by distillation.

The removal of the metal catalyst is carried out, for example, by filtering the reaction mixture directly or after dilution with a solvent. Where necessary, the metal catalyst after filtration may be washed with the same solvent as that used in Step B. The solvent to be used in washing is generally 0.5 to 2 parts by weight, per 1 parts by weight of compound (II).

Then, the obtained filtrate is distilled to obtain compound (I). Alternatively, the obtained filtrate may be distilled after concentration, or after repeating concentration using a solvent (for example toluene) azeotroped with the solvent used in Step B.

EXAMPLES

The present invention is more concretely explained by referring to the following Examples.

The content of compound (I) was measured by a method using gas chromatography (GC).

GC condition: column: Rtx-35 Amine (30 m×0.25 mm, 0.5 μm),

Inj.temperature 200° C., column temperature 50° C. (0 min)→2.5° C./min→125° C. (0 min)∴5° C./min→200° C. (10 min), Det.temperature 210° C. (FID).

Example 1

(3R)-Pyrrolidin-3-ol (60.0 g), 91% paraformaldehyde (23.8 g, 1.05 equivalent on formaldehyde conversion relative to (3R)-pyrrolidin-3-ol), methanol (300.0 g) and 5% platinum on carbon (3.0 g, hydrous, solid content: 1.0 g, platinum amount 0.05 g) were mixed, and the mixture was reacted under condition of hydrogen pressure 0.4 to 0.5 MPa, at 20° C. for 4 hr. The disappearance of (3R)-pyrrolidin-3-ol was confirmed by gas chromatography. To the reaction solution was added diethylamine (5.0 g), and the mixture was reacted under condition of hydrogen pressure 0.4 to 0.5 MPa, at 20° C. for 2.5 hr. After the completion of the reaction, the platinum on carbon was removed by filtration, and washed with methanol (60.00 g), and the obtained filtrate and washing were concentrated. To this concentrate was added toluene (60.00 g), and the mixture was concentrated. To a part (66.3 g) of the obtained concentrate was added again toluene (60.00 g), and the mixture was concentrated to give an oil. This oil was distilled to give a fraction. The yield of (3R)-1-methylpyrrolidin-3-ol was 93%, and the purity thereof was 99.5%.

Example 2

(3R)-Pyrrolidin-3-ol (60.1 g), 93% paraformaldehyde (23.4 g, 1.05 equivalent on formaldehyde conversion relative to (3R)-pyrrolidin-3-ol), methanol (300.1 g) and 5% platinum on carbon (3.7 g, hydrous, solid content: 1.5 g, platinum amount 0.07 g) were mixed, and the mixture was reacted under condition of hydrogen pressure 0.4 to 0.5 MPa, at 20° C. for 6.1 hr. The disappearance of (3R)-pyrrolidin-3-ol was confirmed by gas chromatography. To the reaction solution was added diethylamine (2.5 g), and the mixture was reacted under condition of hydrogen pressure 0.4 to 0.5 MPa, at 20° C. for 3.5 hr. After the completion of the reaction, the platinum on carbon was removed by filtration, and washed with methanol (60.01 g), and the obtained filtrate and washing were concentrated. To this concentrate was added toluene (60.08 g), and the mixture was concentrated. To a part (68.7 g) of the obtained concentrate was added again toluene (59.99 g), and the mixture was concentrated to give an oil. This oil was distilled to give a fraction. The yield of (3R)-1-methylpyrrolidin-3-ol was 86%, and the purity thereof was 97.7%.

Example 3

(3R)-Pyrrolidin-3-ol (60.1 g), 93% paraformaldehyde (23.4 g, 1.05 equivalent on formaldehyde conversion relative to (3R)-pyrrolidin-3-ol), methanol (299.9 g) and 5% platinum on carbon (3.7 g, hydrous, solid content: 1.5 g, platinum amount 0.07 g) were mixed, and the mixture was reacted under condition of hydrogen pressure 0.4 to 0.5 MPa, at 20° C. for 5.7 hr. The disappearance of (3R)-pyrrolidin-3-ol was confirmed by gas chromatography. To the reaction solution was added diethylamine (7.6 g), and the mixture was reacted under condition of hydrogen pressure 0.4 to 0.5 MPa, at 20° C. for 3.4 hr. After the completion of the reaction, the platinum on carbon was removed by filtration, and washed with methanol (60.28 g), and the obtained filtrate and washing were concentrated. To this concentrate was added toluene (60.07 g), and the mixture was concentrated. To a part (68.9 g) of the obtained concentrate was added again toluene (60.06 g), and the mixture was concentrated to give an oil. This oil was distilled to give a fraction. The yield of (3R)-1-methylpyrrolidin-3-ol was 86%, and the purity thereof was 96.5%.

Example 4

(3R)-Pyrrolidin-3-ol (60.1 g), 93% paraformaldehyde (111.5 g, 5.00 equivalent on formaldehyde conversion relative to (3R)-pyrrolidin-3-ol), methanol (300.0 g) and 5% platinum on carbon (3.7 g, hydrous, solid content: 1.5 g, platinum amount 0.07 g) were mixed, and the mixture was reacted under condition of hydrogen pressure 0.4 to 0.5 MPa, at 20° C. for 23.8 hr. The disappearance of (3R)-pyrrolidin-3-ol was confirmed by gas chromatography. To the reaction solution was added diethylamine (201.5 g), and the mixture was reacted under condition of hydrogen pressure 0.4 to 0.5 MPa, at 20° C. for 73.2 hr. After the completion of the reaction, the platinum on carbon was removed by filtration, and washed with methanol (60.07 g), and the obtained filtrate and washing were concentrated. To this concentrate was added toluene (60.14 g), and the mixture was concentrated. To a part (70.3 g) of the obtained concentrate was added again toluene (60.28 g), and the mixture was concentrated to give an oil. This oil was distilled to give a fraction. The yield of (3R)-1-methylpyrrolidin-3-ol was 86%, and the purity thereof was 99.0%.

Example 5

(3R)-Pyrrolidin-3-ol (60.2 g), 93% paraformaldehyde (23.4 g, 1.05 equivalent on formaldehyde conversion relative to (3R)-pyrrolidin-3-ol), methanol (300.8 g) and 5% platinum on carbon (3.7 g, hydrous, solid content: 1.5 g, platinum amount 0.07 g) were mixed, and the mixture was reacted under condition of hydrogen pressure 0.4 to 0.5 MPa, at 20° C. for 6.6 hr. The disappearance of (3R)-pyrrolidin-3-ol was confirmed by gas chromatography. To the reaction solution was added dipropylamine (7.0 g), and the mixture was reacted under condition of hydrogen pressure 0.4 to 0.5 MPa, at 20° C. for 3.6 hr. After the completion of the reaction, the platinum on carbon was removed by filtration, and washed with methanol (60.07 g), and the obtained filtrate and washing were concentrated. To this concentrate was added toluene (60.21 g), and the mixture was concentrated. To a part (69.5 g) of the obtained concentrate was added again toluene (60.25 g), and the mixture was concentrated to give an oil. This oil was distilled to give a fraction. The yield of (3R)-1-methylpyrrolidin-3-ol was 87%, and the purity thereof was 96.5%.

Example 6

(3R)-Pyrrolidin-3-ol (60.0 g), 93% paraformaldehyde (23.4 g, 1.05 equivalent on formaldehyde conversion relative to (3R)-pyrrolidin-3-ol), methanol (300.3 g) and 5% platinum on carbon (3.7 g, hydrous, solid content: 1.5 g, platinum amount 0.07 g) were mixed, and the mixture was reacted under condition of hydrogen pressure 0.4 to 0.5 MPa, at 20° C. for 6.1 hr. The disappearance of (3R)-pyrrolidin-3-ol was confirmed by gas chromatography. To the reaction solution was added diisopropylamine (7.0 g), and the mixture was reacted under condition of hydrogen pressure 0.4 to 0.5 MPa, at 20° C. for 3.6 hr. After the completion of the reaction, the platinum on carbon was removed by filtration, and washed with methanol (60.18 g), and the obtained filtrate and washing were concentrated. To this concentrate was added toluene (60.15 g), and the mixture was concentrated. To a part (69.6 g) of the obtained concentrate was added again toluene (60.42 g), and the mixture was concentrated to give an oil. This oil was distilled to give a fraction. The yield of (3R)-1-methylpyrrolidin-3-ol was 87%, and the purity thereof was 98.2%.

Example 7

(3R)-Pyrrolidin-3-ol (60.1 g), 93% paraformaldehyde (23.4 g, 1.05 equivalent on formaldehyde conversion relative to (3R)-pyrrolidin-3-ol), methanol (300.2 g) and 5% platinum on carbon (3.7 g, hydrous, solid content: 1.5 g, platinum amount 0.07 g) were mixed, and the mixture was reacted under condition of hydrogen pressure 0.4 to 0.5 MPa, at 20° C. for 7.1 hr. The disappearance of (3R)-pyrrolidin-3-ol was confirmed by gas chromatography. To the reaction solution was added butylethylamine (7.0 g), and the mixture was reacted under condition of hydrogen pressure 0.4 to 0.5 MPa, at 20° C. for 4.0 hr. After the completion of the reaction, the platinum on carbon was removed by filtration, and washed with methanol (60.09 g), and the obtained filtrate and washing were concentrated. To this concentrate was added toluene (60.24 g), and the mixture was concentrated. To a part (67.8 g) of the obtained concentrate was added again toluene (60.26 g), and the mixture was concentrated to give an oil. This oil was distilled to give a fraction. The yield of (3R)-1-methylpyrrolidin-3-ol was 88%, and the purity thereof was 98.7%.

Example 8

(3R)-Pyrrolidin-3-ol (60.0 g), 93% paraformaldehyde (23.4 g, 1.05 equivalent on formaldehyde conversion relative to (3R)-pyrrolidin-3-ol), methanol (300.4 g) and 5% platinum on carbon (3.7 g, hydrous, solid content: 1.5 g, platinum amount 0.07 g) were mixed, and the mixture was reacted under condition of hydrogen pressure 0.4 to 0.5 MPa, at 20° C. for 7.5 hr. The disappearance of (3R)-pyrrolidin-3-ol was confirmed by gas chromatography. To the reaction solution was added pyrrolidine (4.9 g), and the mixture was reacted under condition of hydrogen pressure 0.4 to 0.5 MPa, at 20° C. for 3.5 hr. After the completion of the reaction, the platinum on carbon was removed by filtration, and washed with methanol (60.02 g), and the obtained filtrate and washing were concentrated. To this concentrate was added toluene (60.36 g), and the mixture was concentrated. To a part (69.4 g) of the obtained concentrate was added again toluene (60.30 g), and the mixture was concentrated to give an oil. This oil was distilled to give a fraction. The yield of (3R)-1-methylpyrrolidin-3-ol was 88%, and the purity thereof was 98.9%.

Example 9

(3R)-Pyrrolidin-3-ol (60.0 g), 93% paraformaldehyde (23.4 g, 1.05 equivalent on formaldehyde conversion relative to (3R)-pyrrolidin-3-ol), methanol (300.1 g) and 5% platinum on carbon (3.7 g, hydrous, solid content: 1.5 g, platinum amount 0.07 g) were mixed, and the mixture was reacted under condition of hydrogen pressure 0.4 to 0.5 MPa, at 20° C. for 7.5 hr. The disappearance of (3R)-pyrrolidin-3-ol was confirmed by gas chromatography. To the reaction solution was added piperidine (5.9 g), and the mixture was reacted under condition of hydrogen pressure 0.4 to 0.5 MPa, at 20° C. for 3.8 hr. After the completion of the reaction, the platinum on carbon was removed by filtration, and washed with methanol (60.11 g), and the obtained filtrate and washing were concentrated. To this concentrate was added toluene (60.06 g), and the mixture was concentrated. To a part (68.7 g) of the obtained concentrate was added again toluene (60.12 g), and the mixture was concentrated to give an oil. This oil was distilled to give a fraction. The yield of (3R)-1-methylpyrrolidin-3-ol was 88%, and the purity thereof was 97.7%.

Example 10

(3R)-Pyrrolidin-3-ol (60.0 g), 93% paraformaldehyde (23.4 g, 1.05 equivalent on formaldehyde conversion relative to (3R)-pyrrolidin-3-ol), methanol (300.2 g) and 5% platinum on carbon (3.7 g, hydrous, solid content: 1.5 g, platinum amount 0.07 g) were mixed, and the mixture was reacted under condition of hydrogen pressure 0.4 to 0.5 MPa, at 20° C. for 6.3 hr. The disappearance of (3R)-pyrrolidin-3-ol was confirmed by gas chromatography. To the reaction solution was added morpholine (6.0 g), and the mixture was reacted under condition of hydrogen pressure 0.4 to 0.5 MPa, at 20° C. for 4.8 hr. After the completion of the reaction, the platinum on carbon was removed by filtration, and washed with methanol (60.09 g), and the obtained filtrate and washing were concentrated. To this concentrate was added toluene (60.25 g), and the mixture was concentrated. To a part (72.5 g) of the obtained concentrate was added again toluene (60.05 g), and the mixture was concentrated to give an oil. This oil was distilled to give a fraction. The yield of (3R)-1-methylpyrrolidin-3-ol was 89%, and the purity thereof was 96.8%.

INDUSTRIAL APPLICABILITY

According to the present invention, l-methylpyrrolidin-3-ol can be produced on an industrial scale.

The invention claimed is:
1. A method of producing a compound represented by the formula (I):

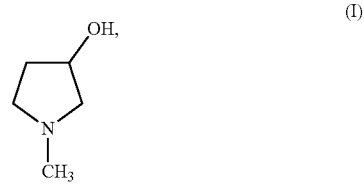

which comprises
Step A: a step of reacting a compound represented by the formula (II):

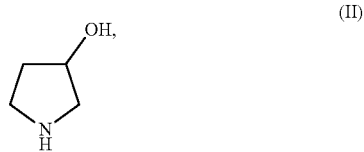

formaldehyde and hydrogen in the presence of a metal catalyst, in a solvent, wherein the amount of the formaldehyde to be used is exceeding 1 mol and not exceeding 5 mol per 1 mol of the compound represented by the formula (II), to obtain a mixture containing the formaldehyde and the compound represented by the formula (I), and
Step B: a step of mixing the obtained mixture containing the formaldehyde and the compound represented by the formula (I) with hydrogen and a secondary amine selected from the group consisting of diethylamine, dipropylamine, diisopropylamine, butylethylamine, pyrrolidine, piperidine and morpholine, in the presence of a metal catalyst, in a solvent, and then removing the metal catalyst, followed by obtaining the compound represented by the formula (I) by distillation.
2. The method according to claim 1, wherein the amount of the secondary amine to be used is (X-1) to (10X-10) mol when the amount of the formaldehyde to be used is X mol per 1 mol of the compound represented by the formula (II).
3. The method according to claim 1, wherein the amount of the formaldehyde to be used is 1.05 to 2.0 mol per 1 mol of the compound represented by the formula (II).
4. The method according to claim 1, wherein the metal catalyst is palladium on carbon or platinum on carbon.

* * * * *